United States Patent
Gallagher (10) Patent No.: US 6,736,801 B1
(45) Date of Patent: May 18, 2004

(54) METHOD AND APPARATUS FOR MONITORING INTRAVENOUS DRIPS

(76) Inventor: George Gallagher, Leigh Cottage, Hiraddug Road, Dyserth, Denbighshire LL18 6HS (GB)

( * ) Notice: Subject to any disclaimer, the term of this patent is extended or adjusted under 35 U.S.C. 154(b) by 0 days.

(21) Appl. No.: 09/622,603

(22) PCT Filed: Feb. 18, 1999

(86) PCT No.: PCT/GB99/00508
§ 371 (c)(1),
(2), (4) Date: Oct. 23, 2000

(87) PCT Pub. No.: WO99/42151
PCT Pub. Date: Aug. 26, 1999

(30) Foreign Application Priority Data

Feb. 18, 1998 (GB) .............................. 9803299

(51) Int. Cl.[7] .............................................. A61M 5/00
(52) U.S. Cl. ........................ 604/253; 604/251; 604/31
(58) Field of Search .................... 604/253, 246–259, 604/30, 31

(56) References Cited

U.S. PATENT DOCUMENTS

| 3,596,515 A | 8/1971 | Cramer | |
|---|---|---|---|
| 4,321,461 A | 3/1982 | Walter, Jr. et al. | 235/92 |
| 4,397,648 A | 8/1983 | Knute | |
| 4,576,592 A | 3/1986 | Danby | 604/80 |
| 4,680,977 A | * 7/1987 | Conero et al. | 73/861.41 |
| 4,822,568 A | * 4/1989 | Tomita | 422/73 |
| 4,884,065 A | * 11/1989 | Crouse et al. | 340/632 |

FOREIGN PATENT DOCUMENTS

| DE | 28 30 512 A | 1/1980 | ............ A61M/5/16 |
|---|---|---|---|
| EP | 0 120 406 A1 | 10/1984 | |
| FR | 2 668 369 A | 4/1992 | ............ A61B/5/168 |
| WO | WO 96 17637 A | 6/1996 | ............ A61M/5/172 |

* cited by examiner

Primary Examiner—Long V. Le
Assistant Examiner—Ann Y. Lam
(74) Attorney, Agent, or Firm—Olson & Hierl, Ltd.

(57) ABSTRACT

A method and apparatus for monitoring intravenous drips by the transmission and detection of a signal, for example a red light, through a fluid flow passage whereby detection of a signal of a given intensity activates an audible or visual indicator. A bracket is attached around a fluid flow passage of the intravenous drip and a signal is transmitted across the passage via optical fibers. The intensity of the signal is detected by a sensor contained within a remote housing.

19 Claims, 7 Drawing Sheets

METHOD AND APPARATUS FOR MONITORING INTRAVENOUS DRIPS

TECHNICAL FIELD

The present invention relates to an improved method and apparatus for monitoring intravenous drips.

BACKGROUND OF THE INVENTION

Intravenous drips are frequently used to administer a continuous flow of fluid to a patient over a given period of time. The drip may administer saline solution to the patient to prevent dehydration and increase blood volume or other fluids, such as insulin, blood or gelofusin. The intravenous drip has a bag containing the fluid which is attached to a filter chamber. This leads to a reservoir which has a piece of tubing extending therefrom which feeds fluid through a needle into the vein of a patient.

The drips are checked at regular intervals by nursing staff to ensure that the fluid is still flowing through the apparatus into the patient. This is time consuming for the nursing staff and additionally, results in the patient being disturbed during the night when the nurse has to check that the drip is still working correctly. Some essential fluids are pumped into the patient via the intravenous drip to ensure that the correct amount of fluid is being administered but the majority of fluids enter by means of gravity, with the bag of fluid being positioned above the height of the patient such that the fluid drips down the tubing and is delivered into the vein of the patient. This necssitates carefuil monitoring of the drip by nursing staff to ensure that sufficient fluid is being administered to the patient.

One direct injection pump is that marketed under the name I-VAC™ which uses a pericycle pump to administer a measured amount of fluid to the patient. This type of pump ensures that the fluid is delivered in the correct dosage to the patient but is only used in life threatening situations for the delivery of essential fluids. This type of pump is expensive and therefore not readily available for use with all patients and furthermore, is very heavy. This is obviously undesirable because the apparatus must be taken with the patient when leaving his hospital bed. The pump is also unsuitable for use in certain departments of the hospital, such as the radiography department, U.S. Pat. No. 4,321,461 (KJW/D Associates) describes a flow rate monitor and totalizing count display apparatus that uses a pulsed infrared light source and receiver and include alarm means for signalling a no-drop condition and for signalling when a preselected count is reached. WO 96/17637 (Midex Marketing Limited) relates to an intravenous infusion flow rate monitoring device that includes a programming console with a data input unit for inputting infusion parameters. The device also includes an alarm unit for indicating when the desired parameters are not being met. However, whilst these devices work effectively they are complex and therefore expensive. They are also difficult and time-consuming to operate.

SUMMARY OF THE INVENTION

It is an aim of the present invention to provide a method and apparatus for monitoring the flow of fluid through an intravenous drip which is lightweight and relatively cheap to manufacture.

It is a further aim of the present invention to provide a method and apparatus for monitoring the flow of fluid through an intravenous drip thereby removing the need for a nurse to frequently check the drip to ensure that the fluid is being administered to the patient.

Yet a further aim of the present invention is to provide a method and apparatus for monitoring the flow of fluid through an intravenous drip which has no detrimental effect on the fluid administered and does not interfere with other equipment which may be operating in the vicinity of the apparatus Accordingly, a first aspect of the present invention provides a method for monitoring the flow of fluid through an intravenous drip comprising the steps of transmitting a signal through a fluid flow passage, detecting the signal transmitted through the passage, monitoring the rate of flow of fluid through the passage from detection of said signals, characterised by the step of setting activation of an audible or visible indicator at a rate corresponding to the rate of flow of fluid through tie passage once a constant rate of flow is achieved wherein detection of a flow rate above and/or below the constant rate activates said indicator.

According to a second aspect of the present invention there is provided an apparatus for monitoring the flow of fluid through an intravenous drip comprising a signal transmitter for tansmitting a signal through a fluid flow passage, a sensor for detecting the signal transmitted through said passage, monitoring means for monitoring the rate of flow of fluid through the passage from detection of signals by said sensor and at least one visible or audible indicator for indicating when the flow rate rises above and/or falls below a constant rate characterized in that the monitoring means includes means for setting activation of said indicator upon achievement of said constant rate.

The signal used in the method and apparatus of the present invention may be infra-red light produced from an infra-red emitter. Alternatively, a red or other light source may be used. Preferably, this signal is transmitted to the intravenous drip by means of an optical fibre. A through-scan, in the form of a bracket, is preferably provided for placement around a region of the intravenous drip for allowing transmission of the beam across the passageway of the flow of fluid. A further optical fibre is preferably attached to the opposite side of the through-scan to receive the signal transmitted through the passage and deliver the signal to the sensor.

The through scan in the form of a bracket is preferably hinged to allow easy placement around a region of the intravenous drip, such as the chamber or drip pod. Adjustable fastenings may be provided to fasten the bracket around the intravenous drip. The bracket may be made of any suitable material but preferably is made of a lightweight plastics material. More preferably, the through-scan is in the form of a C-shaped bracket which is provided with a living hinge to allow the opening in the bracket to be expanded to fit around a region of the intravenous drip and then relaxed such that the bracket grips the drip. Preferably, the C-shaped bracket is provided with two arms extending from the rear thereof, opposite the opening, which may be pressed together to cause divergence of the free ends of the C-shaped bracket. The arms are preferably provided with gripping means on their outer surface. The bracket and arms may be produced as a single moulded plastics unit.

Preferably, a housing, for example in the form of a pocket-sized box is provided for the electronic circuitry, sensor and infrared emitter. The housing is preferably made of a lightweight plastics material. Preferably, the sensor is linked to an indicator in the form of a light emitting diode (LED) which becomes illuminated when the flow of fluid stops. It is preferable that the light emitting diode is visible through the box. Alternatively or additionally, the sensor may be linked to an audible alarm.

In a preferred embodiment of the present invention, the sensor is linked to a bicolour LED which emits a green light when fluid is flowing through the apparatus and changes to a red light when the flow of fluid stops for a predetermined period of time. This change may be achieved when the sensor receives a predetermined amount of energy within a given period of tune indicating that the infra red signal has not been broken by fluid flow. Preferably, the timing is adjustable. The green light may flash with each drip of fluid that passes through the intravenous drip to confirm that the apparatus is working correctly.

Alternatively or additionally, the sensor may be linked to suitable electronic circuitry to allow the number of drops of fluid which are fed from the intravenous drip within a set period of time to be determined, for example drops per minute. Preferably, the number of drops which pass through the apparatus within the set period of time is visible on a display units such as a liquid crstal display (LCD) LED unit provided on the housing or elsewhere.

More preferabley still, the housing is provided with a indicator to demonstrate that fluid is flowing through the drip and a separate display unit, such as an LCD which illustrates the rate of flow of fluid passing through the apparatus. Preferably, the indicator emits a specified colour or other sign when the apparatus is detecting a rate within a specified range of the preset value corresponding to the constant rate. Preferably, the indicator will change to another colour or different sign if the number of drops detected falls below or rises above a predetermined tolerance level, such as ±50% of the preset value corresponding to the constant rate. The indicator may also undergo a corresponding change if no drops are detected within a given period of time.

The apparatus may be powered by means of a battery or mains supply. Preferably, a battery is provided in the housing together with a battery recharger which may be linked to the mains supply. A tricolour LED may be included in the apparatus in place of a bicolour LED, with the third colour of light indicating when the battery is low. Alternatively, a separate indicator may be provided, for example, on the housing, to indicate when the battery is low. The housing is preferably provided with a clip or hook for attachment to the patient, drip stand or elsewhere.

The indicator may also comprise a beacon positioned by the patient or at a nursing station which lights up when the flow of fluid has stopped for a given period of time. Preferably, the beacon is provided on the top of a tall stand. Alternatively, or additionally, a wire may extend from the optical fibre to a glass bulb or light emitting diode which may be placed for example at the top of the drip or drip stand to provide increased visibility of the indicator. The sensor may also be linked to a computer monitor at a nursing station.

The housing may be linkable to an extension lead which may be attached to the optical fibre lead, for example by means of a screw mechanism, to allow an intravenous drip having the through-scan attached thereto to be remote from the housing. This is particularly desirable for when a patient is entering a high risk area, such as a scanning area, whereby the housing may be left outside the area. A receiver, preferably wall mounted, may be provided outside the area for storage of the housing and to allow the drip to be monitored whilst the patient is in the high risk area.

The method and apparatus of the present invention may further provide means for monitoring the amount of fluid which has been administered to a patient. The amount of light which passes through a drop of fluid and the number of drops counted by the sensor within a given period of time may be used to establish the volume of fluid administered, using appropriate calibrations for particular fluids, for example, the number of ml administrated per hour. The volume per hour may be displayed on a display unit, such as an LCD unit provided on the housing or elsewhere. A computer may collect data for a large number of intravenous drips which may be displayed on a computer screen.

BREIF DESCRIPTION OF THE DRAWINGS

For a better understanding of the present invention and to show more clearly how it may be carried into effect, reference will now be made by way of example only, to the accompanying drawings in which.

DETAILED DESCRIPTION OF THE DRAWINGS AND PREFERRED EMBODIMENTS

Figures 1, 2:
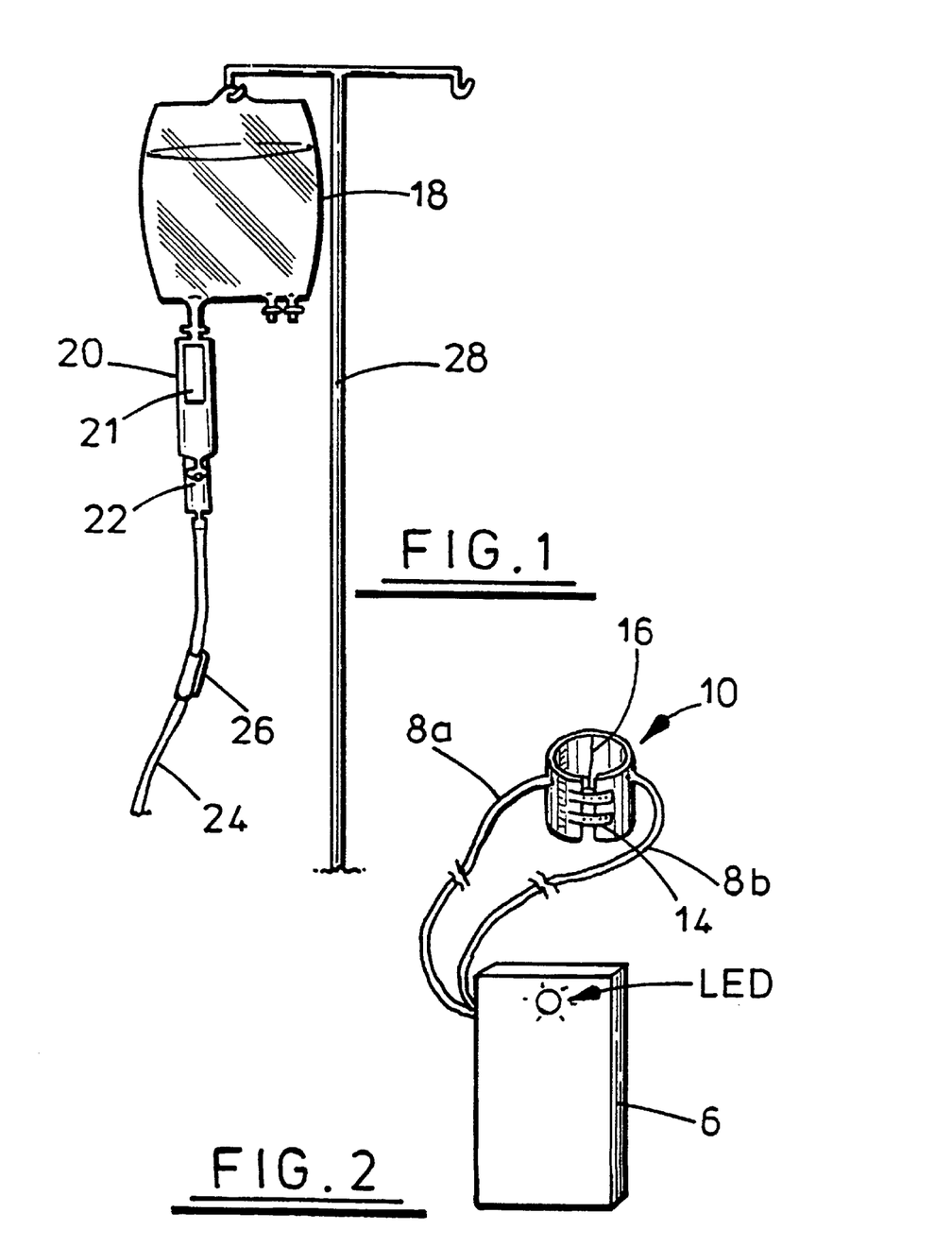
FIG. 1 is a schematic diagram of a conventional intravenous drip.
FIG. 2 is a schematic diagram of an apparatus according to one embodiment of the present invention.

Referring to FIG. 1 of the accompanying drawings, a standard intravenous drip for administering fluid to a patient is illustrated. The fluid F, such as saline solution, is stored in a bag 18 which is attached to a chamber 20 containing a filter 21. This is linked to a reservoir 22 having a length of tubing 24 extending therefrom which delivers fluid to a needle (not shown) which is inserted into a vein of a patient. The rate of flow of the fluid through the tubing may be altered by adjusting the ball valve 26. Generally, the bag 18 is hung from a drip stand 28 by the patient's bed and a nurse checks the drip at regular intervals to ensure that the required fluid is being delivered to the patient. If the patient moves away from the bed, the drip must remain attached to the patient and hence, the drip is transported with the patient by the provision of wheels (not shown) on the base of the stand.

Figure 3:
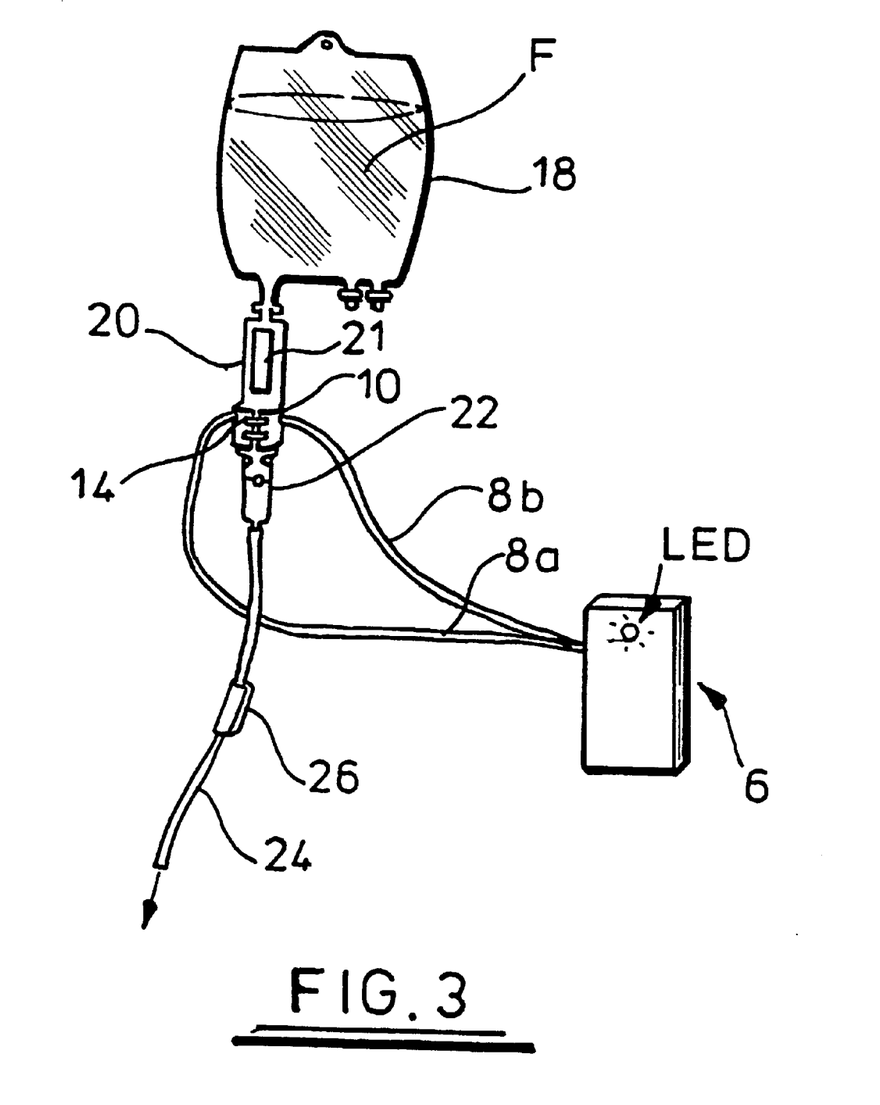
FIG. 3 is a schematic diagram of the apparatus shown in FIG. 2 attached to the intravenous drip shown in FIG. 1.

FIGS. 2 and 3 of the accompanying drawings show one embodiment of an apparatus according to the present invention for monitoring the flow of fluid through an intravenous drip. The apparatus uses a beam of infra red light to detect a drip of fluid passing through the chamber 20 of the intravenous drip. The apparatus comprises a portable housing, in the form of a box 6, which contains an infra red emitter and various electronic circuitry, such as a sensor, ganged relay and timer.

The infra red emitter transmits a beam of infra red light along an optical fibre 8a to a through-scan 10 in the form of a bracket. The bracket illustrated is dimensioned to fit around the chamber 20 of the intravenous drip but may be constructed to fit around another region of the drip, if desired. The bracket is provided with a hinge 16 and adjustable fastenings 14 to allow the through-scan to be attached to chambers of various sizes. The box and bracket may be made of any suitable material but preferably are made of a lightweight plastics material by conventional moulding techniques.

A second optical fibre 8b extends from the opposite side of the bracket 10 such that a path of light may travel from fibre 8a, through the chamber to fibre 8b for delivery back to the box 6 and detection by the sensor contained within the box. It is to be appreciated that the entry into and exit from the through-scan must be perfectly aligned to allow accurate transmission of the signal to provide a viable reading. The circuit is unbroken when no fluid passes through the chamber but is broken as soon as a drop of fluid passes from the bag 18 into the chamber 20 and to the reservoir 22. In this manner, the continual transmission of a beam of high light intensity to the sensor may be used to detect that the flow of liquid through the drip has stopped and hence, that the fluid is no longer being delivered to the patient.

Figure 4:
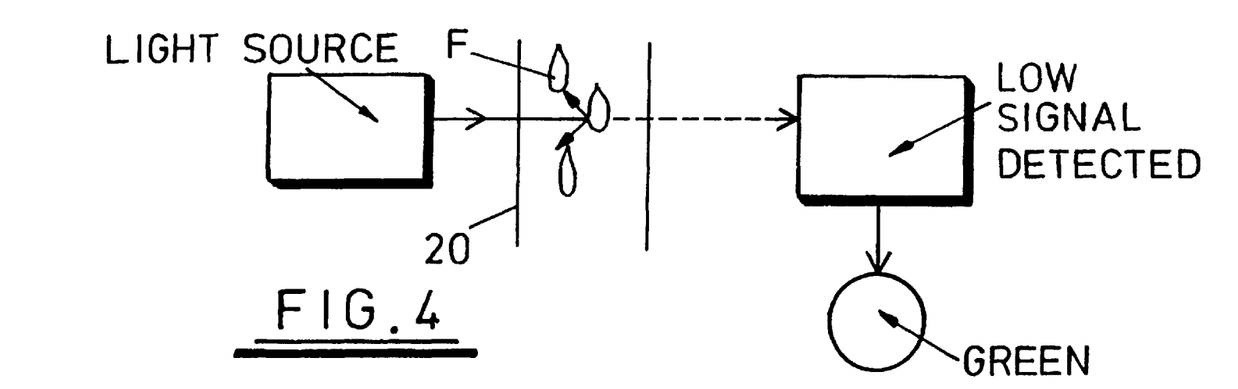
FIG. 4 is a block diagram of the basic sequence of steps for emitting a green light using the apparatus of the present invention.
Figure 5:
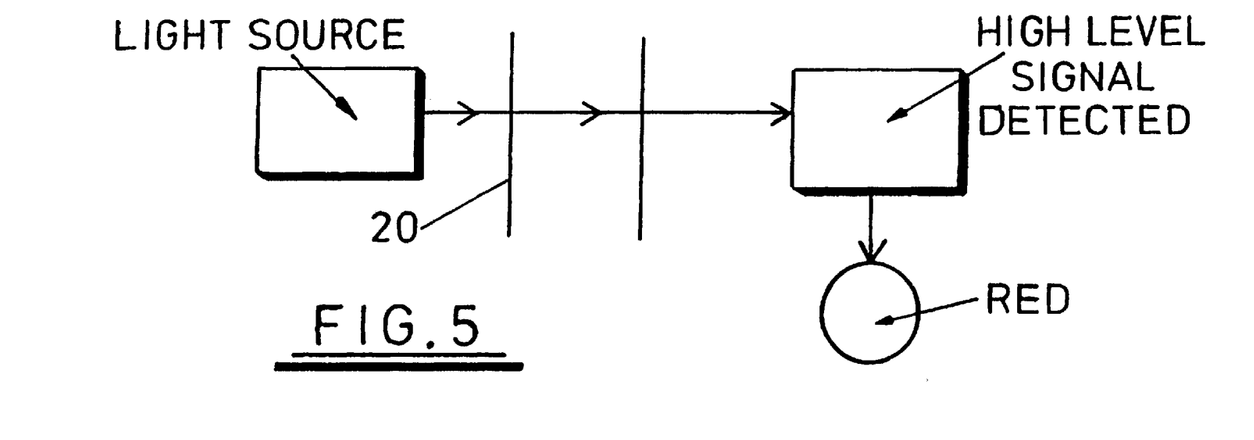
FIG. 5 is a block diagram of the basic sequence of steps for emitting a red light using the apparatus of the present invention.

The sensor is preferably linked to a circuit which has a light emitting diode (LED) which becomes illuminated when the flow of fluid stops. Preferably, a bicolour LED is provided which emits a green light when fluid is flowing through the apparatus and a reduced amount of infra red light is being received by the sensor (see FIG. 4 of the accompanying drawings) which changes to red when the flow of fluid stops. This change is brought about when a predetermined amount has energy has built up over a given period of time, for example 10 seconds, indicating that the infra red signal has not been broken by a drip of fluid, as shown in FIG. 5. Circuitry may be installed such that the green light flashes with each drip of fluid that passes through the chamber to confirm that the apparatus is working correctly.

Figure 6:
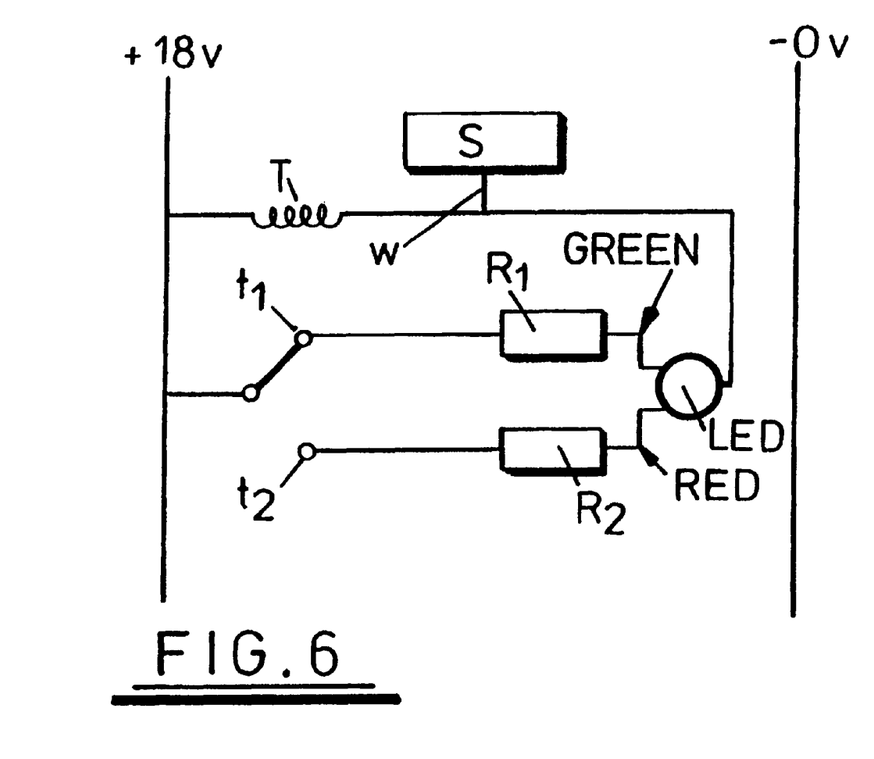
FIG. 6 is a diagram of the circuitry that may be contained in the box of the apparatus shown in FIGS. 1 and 2.

FIG. 6 of the accompanying drawings shows an example of the circuitry which may be employed in the apparatus of the present invention for effecting the required response from the sensor. The sensor S is energised by receiving the infra red light which has been transmitted through the optical fibres 8a and 8b. A negative switching wire W runs from the sensor to a timer coil T and also to one side of a bicolour LED. When the power is switched on, the beam reaching the sensor is unbroken by the flow of fluid which causes a signal to be transmitted through the negative switching wire in energise the timer coil T which is set to run for a predetermined period of time. In the normal state, the wire leads through timer contact $TC_1$ to result in illumination of the green side of the LED. However, if the timer T reaches the end of its cycle without receiving a further signal, the timer contact $TC_1$ is broken and timer contact $T_2$ closes thereby causing the red side of the LED to be illuminated to indicate that no fluid has passed through the drip during a complete cycle of the timner. If fluid does flow through the apparatus, this is detected by a reduced intensity of light reaching the sensors which results in the transmission of a signal to the timer T to reset the coil to the beginning of its cycle. Thus, if drips of fluid keep passing through the apparatus, the timer T will be continually reset and the light will remain green. Resistors $R_1$ and $R_2$ are provided to reduce the intensity of the current passing through the LED.

The electronic circuitry for use in the apparatus of the present invention is minimal and fits easily in the small box 6 having the LED visible on a side thereof. The infra red emitter may be contained within the box and a battery for providing power to the system may also be situated therein. Generally, a battery of at least 12–30 v will be required to ensure sufficient energy is supplied to the sensor. Preferably, circuitry having a low current demand is employed in the apparatus. The light emitting diode may be a tricolour LED with the illumination of a third colour, such as amber, indicating that the battery is low. Optionally, a battery recharger may be included within the box for lining to a mains supply to recharge the battery, for example, whilst the patient is in bed asleep. The box may be provided with a clip to allow convenient attachment to the drip stand or to the patient.

Additionally, the circuitry may be linked to a beacon positioned by the bed of the patient or at a nursing station which lights up or flashes when the flow of fluid through the drip stops for a given period of time. This will be readily visible to the nursing staff who may then adjust the drip accordingly. Additionally or alternatively, the sensor may be linked to computer monitors provided at a nursing station which may be checked at regular intervals by the nursing staff without disturbing the patients. The apparatus may also give out an audible alarm if an intravenous drip has stopped administering fluid to alert the nursing staff.

The amount of fluid administered to the patient may also be monitored using the method and apparatus of the present invention. The amount of light which passes through a drop of fluid and is detected by the sensor may be used to establish the volume of fluid administered using the appropriate calibrations. Each monitor could collect data for a large number of drips and thereby provide an accurate record of the fluids which are being given to a large number of patients.

It is to be appreciated that an alternative light signal may be used in the method and apparatus of the present invention instead of infra red, such as a beam of red light.

Figure 7:
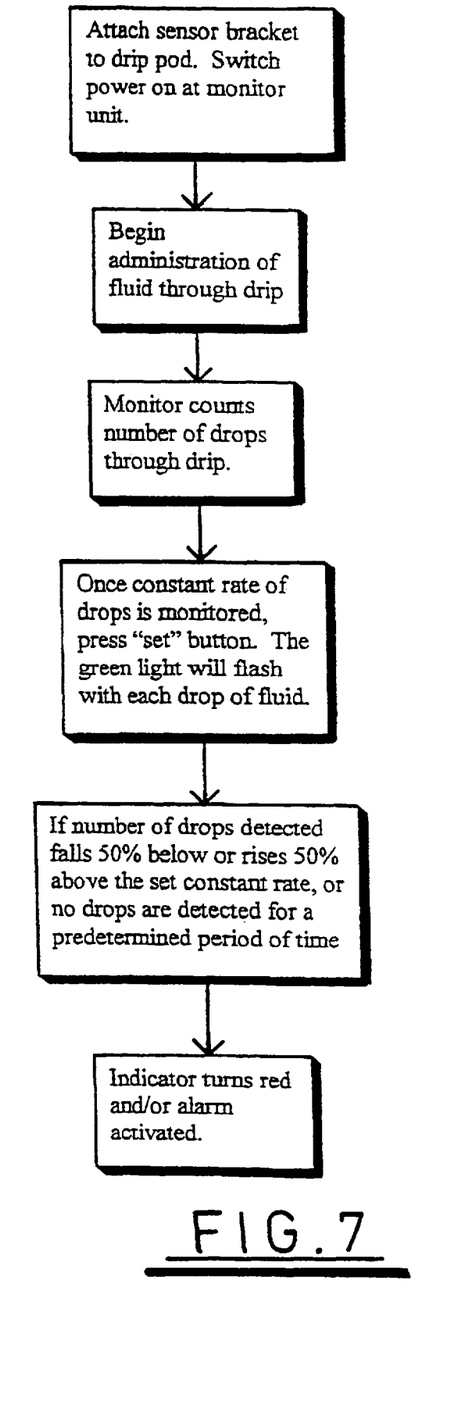
FIG. 7 is a flow diagram of the sequence of steps in a further embodiment of the method of the present invention.
Figures 8, 9:
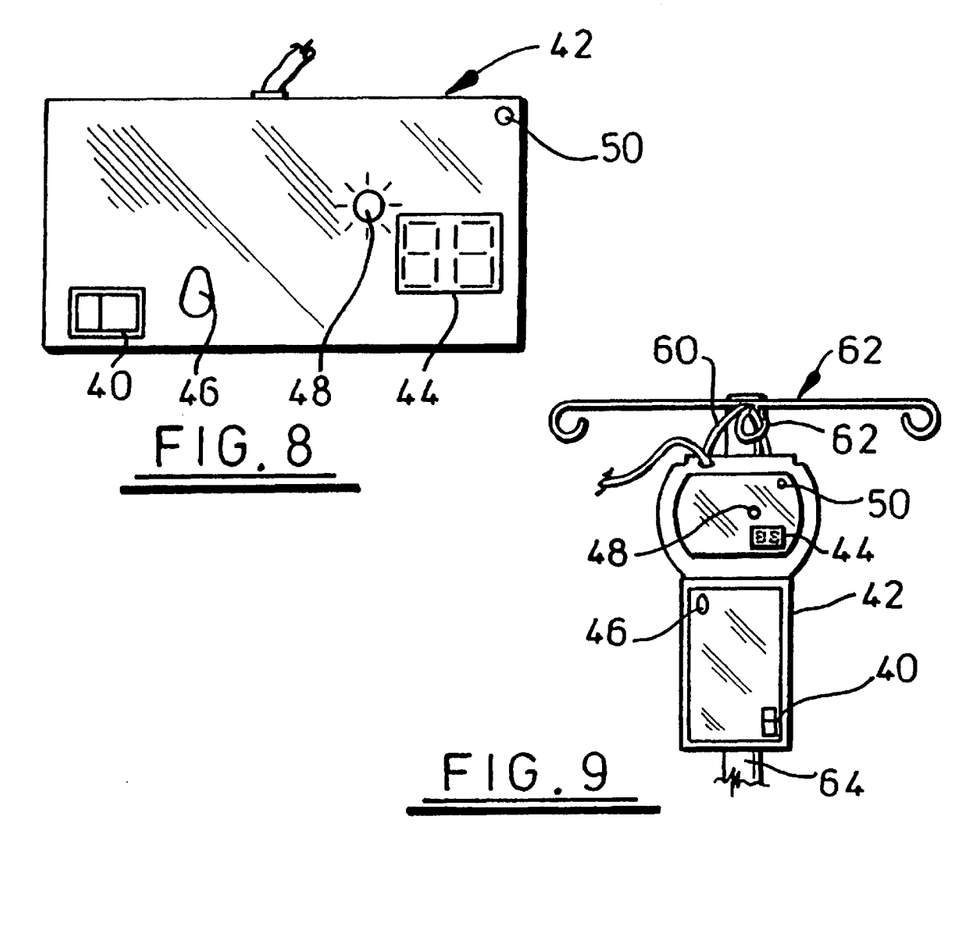
FIG. 8 is a schematic diagram of a housing of the apparatus according to another embodiment of the present invention.
FIG. 9 is a schematic diagram of a housing of the apparatus according to yet a further embodiment of the present invention.

Referring to FIGS. 7 and 8 of the accompanying drawings, another embodiment of the method and apparatus of the present invention is illustrated in which the apparatus may be set at a particular rate of flow of fluid through the intravenous drip and has means for activation of a visual and/or audible alarm should the measured rate fall below or rise above a predetermined tolerance level of the preset value.

The sensor bracket or clip is attached around the chamber or drip pod of the intravenous drip as hereinbefore described and the apparatus is switched on by means of the power switch 40 provided on the monitor unit or housing 42 (see FIG. 8). The administration of the fluid through the drip is commenced and the monitor detects the drips by means of the breakage of a beam of light which is transmitted through the chamber. The monitor unit 42 is able to detect the rate of flow of liquid through the chamber (for example, in drips per minute or ml per hour) and provides a reading on an LCD unit 44 provided on the housing. For example, generally twenty drips of clear fluid corresponds to 1lnl of liquid being administered. More viscous liquids such as blood, require fifteen drips to administer 1lni of fluid. This can be used to determine the amount of fluid administered per minute or hour. Once the desired rate is achieved and becomes constant, the "set" switch 46 provided on the monitor unit is pressed such that the unit is set at the desired rate. A clear indicator 48 is illuminated in green when the rate detected by the monitor unit falls within a predetermined tolerance of the set rate, for example ±50%. If the rate falls outside the tolerance level or if no drops are detected within a predetermined period of time, the clear indicator turns red and/or an audible alarin is activated.

The clear indicator also flashes when drips are passing through the chamber to demonstrate that the apparatus is functioning correctly as hereinbefore described. Additionally, a low power indicator 50 is provided on a monitor unit.

FIG. 9 of the accompanying drawing illustrates an alternative design for the monitor unit of the present invention. Identical features already described in relation to FIG. 8 are given the same reference numerals. The monitor unit is attached by a hook 60 to a branch 62 of the drip stand 64.

Figure 10A:
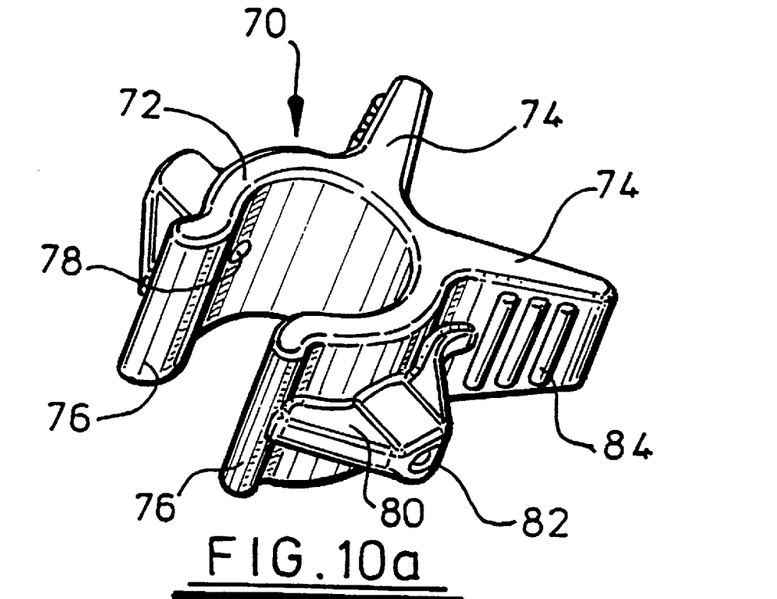
FIGS. 10a to 10c illustrate a preferred embodiment of a through-scan for the apparatus of the present invention.
Figure 10B:
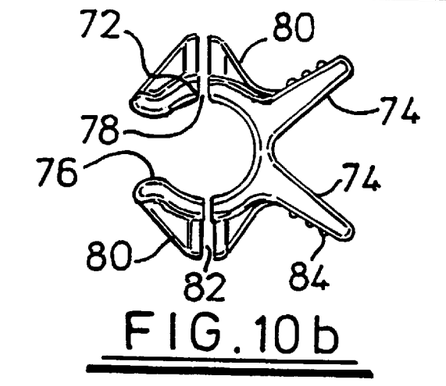
Figure 10C:
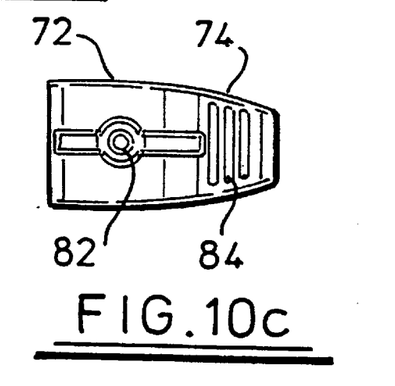

Referring to FIGS. 10a to 10b of the accompanying drawings, a preferred embodiment for the through-scan bracket 70 is illustrated. The through-scan 70 is in the form of a C-shaped bracket or clip 72 having two arms 74 extending obliquely from the rear thereof. The arms 74 may be pressed together to cause divergence of the free ends 76 of the C-shaped bracket thereby enabling the bracket 70 to be slotted onto the drip pod, or chamber (not shown). Releasing pressure from the arms 74 causes the bracket to relax and grip the chamber. This is achieved by means of a living hinge provided in the central rear section of the bracket (not shown) or forming the bracket from a reinforced elastomeric material to allow the bracket to resume its original shape after being distorted to fit around the chamber.

Through-holes 78 are provided through opposite sides of the C-shaped bracket to allow passage of the beam of light. Protrusions 80 extend from the holes for connection of the optical fibre to the bracket and have a corresponding channel 82 therethrough. The arms of the bracket are also provided with gripping means on their outer surface, such as ribbing 84.

A number of further accessories may be provided for use with the apparatus of the present invention, such as a receiver unit for supporting the monitor unit or housing which may be, for example, wall mounted. A coiled extension lead may also be provided to allow the bracket and intravenous drip to be located a distance from the monitor unit. This enables the intravenous drip to be taken into high risk areas, such as scanning rooms, and the monitor may be left outside. Additionally, a lead may run from the optical fibre to a glass bulb or LED located at a convenient site, such as the top of the drip or drip stand, for example, being placed through the eye provided in the fluid bag of the intravenous drip.

A transmission of a light signal across a through-scan via optical fibres has not previously been used for detecting dripping fluids, such as saline solution and it is surprising that good results are achieved for transparent liquids. The use of an infra-red or other light signal, such as red light is desirable for hospital equipment since the beam of light has no detrimental effect on the fluid being administered and does not effect any other apparatus which may be operating in the vicinity of the intravenous drip. For this reason, equipment which utilises such signals do not require permission before being used in hospitals whereas all other signals, such as radiation, do have to be tested to conform with specific legislation.

Additionally, the provision of the electronic circuitry remote from the through-scan has a number of advantages. The bracket is cheaper and easier to manufacture and maintain if the electronics are not contained in the walls of the bracket. It is much cheaper to house the components on a circuit board within the housing than provide them within the bracket. The bracket is also lighter and may be taken into high risk scanning areas without any of the accompanying circuitry.

The components used in the apparatus of the present invention are relatively cheap compared to other hospital equipment, such as pericycle pumps. The apparatus is also small, compact and lightweight thus making it suitable for transportation by the patient. The apparatus may also be taken into most hospital departments, such as the radiography department, which is not possible with other devices which can interfere with radiation.

The ability to check and monitor an intravenous drip without the necessity of a nurse having to physically look at the tubing to see that fluid is flowing through the drip will reduce the high work load of nursing staff in a service sector where funds are limited and there is a shortage of trained staff. Additionally, the patient is not inconvenienced by the nurse having to frequently check the drip, particularly through the night.

What is claimed is:

1. An apparatus for monitoring the flow of intravenous fluid passing as drops through a fluid flow passage comprising:
    a signal transmitter including a first optical fiber for transmitting a signal from said signal transmitter through said passage and said fluid passing therethrough;
    a signal sensor including a second optical fiber for detecting signals so transmitted through said passage;
    a monitor subassembly responsive to signals so detected by said signal sensor for monitoring the rate of flow of said fluid through said passage by detection of interruptions in transmissions of said so transmitted signal due to fluid dripping through said passage, said monitor subassembly having at least one visible or audible indicator for indicating when said rate of flow rises above or falls below a predetermined constant rate, and said monitor subassembly having an adjustable setting component for setting activation of said indicator upon achievement of said constant rate; and
    a bracket associated with said signal transmitter and with said signal sensor for placement around a region of said passage and for allowing said signal transmitting and said signal detecting through said passage;
    said bracket including a hinge adjustment component for transversely enlarging and contracting an interior region of said bracket thereby allowing placement of said bracket about said passage at said regon.

2. The apparatus of claim 1 wherein the said first optical fiber is terminally connected to said bracket at a first bracket location, and said second optical fiber is terminally connected to said bracket at a second bracket location, and said first and said second bracket locations are generally in opposed relationship to each other across said region whereby said signal is transmitted to and from said passage by said first and said second optical fibers.

3. The apparatus of claim 1 wherein said bracket is comprised of an elastomeric material, C-shaped, has an opening defined therein, and has two arms extending obliquely and outwardly from a rearward portion thereof that is generally opposite said opening, whereby, when said arms are pressed towards one another, said bracket opening is enlarged, thereby facilitating placement and location of said bracket around said passage at said region.

4. The apparatus of claim 1 wherein a remote housing is provided for containing components comprising said monitor subassembly, associated electronic circuitry, said signal transmitter excluding said first optical fiber, and said signal sensor excluding said second optical fiber.

5. The apparatus of claimed in claim 1 wherein said indicator is a light emitting diode.

6. The apparatus of claim 5 wherein said light emitting diode flashes with each drop of said fluid which passes through said passage.

7. The apparatus of claim 1 wherein said monitor includes electronic means for allowing the rate of flow of fluid through said passage to be measured and the rate so measured is displayed on a display unit.

8. The apparatus of claim 1 wherein said indicator is a light emitting diode that emits a specified color when said rate of flow falls within a specified range of said constant rate and changes to another color when said rate of flow falls below or rises above a predetermined level of said constant rate.

9. The apparatus of claim 1 wherein said monitor subassembly further includes a beacon which is illuminated when said rate of flow of fluid through said passage has risen above or fallen below a preset value.

10. The apparatus of claim 1 wherein said monitor subassembly further includes means for measuring the volume of fluid passing through said passage in a predetermined time interval.

11. Apparatus for monitoring the rate of flow of fluid that passes as sequential drops through a tubular vessel having wall portions that transmit light signals, said apparatus comprising in combination:

(a) a bracket for disassociatable association around a region of said vessel, said bracket including a hinge adjustment component for transversely enlarging and contracting the interior region of said bracket, thereby allowing placement of said bracket about said vessel at said region;

(b) a light signal generator for emitting a light signal;

(c) a first optical fiber for conveying said light signal from said signal generator to said bracket, and said first optical fiber having a terminal fiber region associated with said bracket for transmitting said so conveyed light signal through said vessel at said region;

(d) a light signal-sensor for receiving light signals;

(e) a second optical fiber for conveying light signals from said bracket to said light signal sensor, said second optical fiber having a terminal fiber region associated with said bracket for receiving said light signals so transmitted through said vessel and said second optical fiber being for conveying said so received light signals, said respective terminal fiber regions of said first and said second optical fibers being in a light signal aligned relationship relative to each other across said region so that with said light signals so transmitted through said vessel are so received by said second optical fiber whereby said drops so passing through said vessel move through said so transmitted light signals;

(f) a monitor subassembly responsive to signals so detected by said signal sensor for monitoring the rate of flow of said fluid through said passage by detection of interruptions in transmissions of said so transmitted signal due to fluid dripping through said passage, said monitor subassembly having at least one visible or audible indicator for indicating when said rate of flow rises above or falls below a predetermined constant rate, and said monitor subassembly having an adjustable setting component for setting activation of said indicator upon achievement of said constant rate; and (g) a housing remotely located relative to said bracket for housing said signal generator, said signal sensor, and said monitor subassembly.

12. The apparatus of claim 11 wherein said indicator includes a light emitting diode that emits a visible light.

13. The apparatus of claim 11 wherein said indicator includes a liquid crystal display.

14. The apparatus of claim 11 wherein said indicator includes a bicolor light emitting diode that shows one color representative of the fluid flow situation where no drop passes through said region of so transmitted light signals in a predetermined time interval, and another color representative of the fluid flow situation where at least one of said sequential drops passes through said region of so transmitted light signals in a predetermined time interval.

15. The apparatus of claim 11 wherein said monitor subassembly includes adjustable settable fluid flow rate selecting means for selecting and monitoring a set rate of fluid flow through said vessel.

16. The apparatus of claim 15 wherein, after said adjustable settable fluid flow rate selecting means is so set, said indicator indicates a signal if the number of drops passing therethrough is within a selected range that includes said set rate.

17. The apparatus of claim 16 wherein said selected range is within about 50% of said set rate.

18. The apparatus of claim 15 wherein, after said adjustable settable rate selecting means is so set, said indicator indicates a signal if the number of drops passing through said vessel is outside of a selected range that includes said set rate.

19. The apparatus of claim 17 wherein said selected range is within about 50% of said set rate.

* * * * *

UNITED STATES PATENT AND TRADEMARK OFFICE
CERTIFICATE OF CORRECTION

PATENT NO.    : 6,736,801 B1
DATED         : May 18, 2004
INVENTOR(S)   : George Gallagher It is certified that error appears in the above-identified patent and that said Letters Patent is hereby corrected as shown below:

Column 1,
Line 31, change "necssitates" to -- necessitates --.
Line 46, change "KJW/D" to -- K/W/D --.

Column 2,
Line 18, change "tie" to -- the --.
Line 45, change "through scan" to -- through-scan --.

Column 3,
Line 21, change "units" to -- unit, --.

Column 5,
Line 11, insert a space after "and".
Line 56, insert -- w -- after "wire"; and delete "in", insert -- to --.
Lines 58, delete "$TC_1$" insert -- $t_1$ --.
Line 61, delete "$TC_1$" insert -- $t_1$ --; and delete "$T_2$" insert -- $t_2$ --.

Column 6,
Line 17, delete "lining" insert -- linking --.
Lines 65 and 67, delete "1lnl" insert -- 1ml --.

Column 7,
Line 10, delete "alarin" insert -- alarm --.
Line 29, insert -- 70 --.

Column 8,
Line 67, insert -- is generally --.

UNITED STATES PATENT AND TRADEMARK OFFICE
CERTIFICATE OF CORRECTION

PATENT NO. : 6,736,801 B1
DATED : May 18, 2004
INVENTOR(S) : George Gallagher It is certified that error appears in the above-identified patent and that said Letters Patent is hereby corrected as shown below:

<u>Column 9,</u>
Line 12, delete "claimed in".

Signed and Sealed this

Twenty-first Day of February, 2006

JON W. DUDAS
*Director of the United States Patent and Trademark Office*